(12) United States Patent
Hills et al.

(10) Patent No.: US 6,824,761 B1
(45) Date of Patent: Nov. 30, 2004

(54) ANTI-ASTHMATIC COMBINATIONS COMPRISING SURFACE ACTIVE PHOSPHOLIPIDS

(75) Inventors: Brian Andrew Hills, Alexandra Hills (AU); Derek Alan Woodcock, Berkhampstead (GB); John Nicholas Staniforth, Bath (GB)

(73) Assignee: Britannia Pharmaceuticals Limited, Redhill (GB)

( * ) Notice: Subject to any disclaimer, the term of this patent is extended or adjusted under 35 U.S.C. 154(b) by 0 days.

(21) Appl. No.: 09/856,400

(22) PCT Filed: Nov. 26, 1999

(86) PCT No.: PCT/GB99/03952

§ 371 (c)(1),
(2), (4) Date: Sep. 17, 2001

(87) PCT Pub. No.: WO00/30654

PCT Pub. Date: Jun. 2, 2000

(30) Foreign Application Priority Data

May 28, 1999 (GB) ............................................. 9912639

(51) Int. Cl.[7] ............................. A61K 9/12; A61K 9/14; A61K 9/127

(52) U.S. Cl. ............................. 424/45; 424/46; 424/43; 424/489; 424/450; 514/826; 514/851

(58) Field of Search ............................... 424/45, 43, 46, 424/489, 450; 514/851, 826

(56) References Cited

U.S. PATENT DOCUMENTS

| | | | |
|---|---|---|---|
| 4,828,844 A | | 5/1989 | Röntgen-Odenthal et al. ... 424/489 |
| 4,895,719 A | * | 1/1990 | Radhakrishnan et al. ..... 424/45 |
| 5,306,483 A | * | 4/1994 | Mautone ...................... 424/45 |
| 5,698,537 A | | 12/1997 | Pruss ........................... 514/78 |
| 5,925,334 A | * | 7/1999 | Rubin et al. .................. 424/45 |
| 6,482,391 B1 | | 11/2002 | Hills et al. .................... 424/45 |

FOREIGN PATENT DOCUMENTS

| | | |
|---|---|---|
| DE | 32 29 179 A1 | 2/1984 |
| EP | 0 260 241 A1 | 3/1988 |
| EP | 0 528 034 A1 | 2/1993 |
| EP | 0 689 848 A1 | 1/1996 |
| JP | 58 164513 | 9/1983 |
| WO | WO 87/05803 | 10/1987 |
| WO | WO 91/16882 | 11/1991 |
| WO | WO 96/19199 | 6/1996 |
| WO | WO 96/22764 | 8/1996 |
| WO | WO 97/29738 | 8/1997 |
| WO | WO 99/00134 | 1/1999 |
| WO | WO 99/27920 | 6/1999 |
| WO | WO 99/33472 | 7/1999 |
| WO | WO 00/30654 | 6/2000 |

OTHER PUBLICATIONS

Morley et al., "Physical and physiological properties of dry lung surfactant," *Nature*, 271(5641):162–163, 1978.

Sorkness et al., "A double–blind, randomized, placebo–controlled study of single, nebulized doses of Exosurf™ (EXO) in patients with mild to moderate asthma," *J. Allergy Clin. Immunol.*, 95(1,2):352, 1995; Abstract only.

Takahashi et al., "Biophysical properties of protein–free, totally synthetic pulmonary surfactants, ALEC and Exosurf, in comparison with surfactant TA," *ACTA Paediatrica Japonica*, 36:613–618, 1994.

International Search Report for PCT/GB 99/03952 (WO 00/30654), mailed Mar. 3, 2000.

Co–pending application Ser. No. 09/555,734, filed Jun 2, 2000, U.S. Counterpart to PCT/GB98/03543 (WO 99/27920).

* cited by examiner

*Primary Examiner*—Thurman K. Page
*Assistant Examiner*—Mina Haghighatian

(57) ABSTRACT

Disclosed is a combination product for use in treating asthma and other respiratory conditions comprising a medicament comprising a surface active phospholipid composition in the form of a fine powder and an antiasthma drug. The product is arranged to be administered to the lungs by inhalation, for example, by the disclosed devices.

23 Claims, 2 Drawing Sheets

ANTI-ASTHMATIC COMBINATIONS COMPRISING SURFACE ACTIVE PHOSPHOLIPIDS

The present application is a nationalization of International Patent Application PCT/GB99/03952, filed Nov. 26, 1999, which claims priority to British Patent Application 9912639.3, filed May 8, 1999 and to International Patent Application PCT/GB98/03543, filed Nov. 26, 1998.

FIELD OF THE INVENTION

This invention relates to pharmaceutical products for use in the treatment of asthma and to deliver devices including the products.

This invention relates to pharmaceutical products for use in the treatment of asthma and to delivery devices including the products.

It has been estimated that asthma affects between 4 and 10 percent of the population, causing distress and alarm to both sufferers and bystanders. Asthma attacks appear to be precipitated in many cases by a number of factors such as exercise or pollutants in the inspired air. Other agents such as pollen and airborne particles may predispose an asthma sufferer to an attack by sensitising the airways. This has led to the belief that effective treatment should include administration of drugs which reduce the sensitivity of asthma sufferers to allergens or which neutralise the allergic reaction.

The lungs and airways of non-asthmatics may contain a natural protective barrier which prevents pollutants and other potential irritants from reaching receptors which would otherwise produce an acute attack. Studies have suggested that it is possible to simulate in the lungs of asthma sufferers the situation in normal lungs by causing surface-active phospholipids (SAPL) to bind to the tissue surface of the lungs, thereby reducing the number of receptors exposed to noxious stimuli and reducing the bronchoconstrictor reflex.

SAPLs are used clinically for the treatment of respiratory distress syndrome (RDS) in neonates. In this role, it has been assumed that the SAPL functions by reducing the high surface tension forces at the air-water interface within the alveoli, thereby reducing the pressure needed to expand the lungs, see Bangham et al., Colloids & Surfaces, 10 (1984), 337 to 341. Thus, commercially available formulations of SAPL have been designed co spread rapidly over an air-aqueous interface, thereby reducing what is otherwise a very high surface tension of water.

Limited clinical studies have been carried out to determine the effect of commercial SAPLs marketed for treatment of RDS in neonates on asthmatic subjects,—see Kurashima et al Jap. J. Allergol 1991; 40, 160. This paper reported some amelioration of bronchoconstriction in asthmatic adults using an SAPL obtained by extraction from bovine lungs. In another study on children, also using an SAPL obtained from bovine lungs, no significant changes in lung function or histamine response were found,—see Oetomo et al—American Journal of Respiratory and Critical Care Medicine 153; 1996, page 1148.

EP 0 528 034A describes the use of pulmonary surface active material as an ingredient of an antiasthmatic, which is in the form of a liquid or suspension for injection or spraying into the patient's air way.

The invention provides a therapeutic combination product for use in the prevention and/or treatment of asthma comprising (a) a medicament comprising a surface active phospholipid (SAPL) composition in finely divided form, the SAPL including a component which enhances spreading of the medicament over a surface at about normal mammalian body temperature; and b) an antiasthma drug;

wherein ingredients (a) and (b) are provided in a form for administration together or separately.

It is believed that the finely divided powder of ingredient (a), which preferably comprises at least first and second components, has two important effects:

First, the medicament (a) has surfactant properties, which enable it to spread rapidly over the surfaces of the lungs and air passages. It is an important feature of the present invention that the medicament (a) is in the form of a powder, that is, it is in solid form. The "dry" surfactant has a high surface activity. It is believed that, on contact of a first component of the medicament (a) with the mucous within the lungs, the presence of a second component results in a lowering of the melting point of the first component, promoting rapid spreading of the first component over the liquid-air interface as a thin film at body temperature. For example, the normal melting temperature of dipalmitoyl phosphatidyl choline, which is a preferred first component is about 40° C., that is, above the normal body temperature. When used in combination with a suitable second component, such as a phosphatidyl glycerol, however, the melting point of the dipalmitoyl phosphatidyl choline can in effect be reduced to below the normal body temperature.

Second, once the surface active medicament is in situ over the surfaces of the lungs and air passages, a component of the composition is thought to migrate across the mucous layer enabling a thin hydrophobic lining or coating co be adsorbed onto the tissue surface. Thus, over and above the surface tension reducing properties mentioned above the medicament of the invention is believed to provide a protective effect by virtue of the adsorbed layer in binding to the epithelium, the phospholipid may mask the irritant receptors which elicit the bronchorestrictor reflex, that is, which cause narrowing of the bronchi.

The medicament (a) is in finely divided solid form. It is believed that, as a consequence of the high surface activity of medicament (a) in that form there results a significant drop in surface tension on contact with the aqueous mucous layer of the lung, giving enhanced effectiveness of ingredient (a) and permitting improved access to the lung surfaces for the antiasthma drug(s) to be administered. Thus, the use of the medicament (a) in combination with an antiasthma drug is believed to enhance the effectiveness of the antiasthma drug.

Moreover, as mentioned above, the binding of the phospholipid component to the lung surface is believed to reduce bronchorestrictor as a consequence of a reduction, in receptor-mediated activity attributable to the masking of irritant receptors. That reduced bronchorestriction acts cumulatively with the anti-bronchorestrictive activity of the antiasthma drug. Thus, in some circumstances it may be possible for dosages of an antiasthma drug to be administered to a given patient to be reduced, as a consequence of the synergistic effect of medicament (a) in enhancing the effectiveness of the antiasthma drug as well as the additional anti-bronchorestrictive activity of medicament (a) itself.

"Finely divided" as used herein means that the material has a particle size distribution which is such that at least a major proportion by weight of the particles are small enough to enter into a patient's airways and, preferably, deep into the lungs when inhaled. In practice, the first and second components preferably each have a particle size distribution which is such that not less than 90%, by weight, of the particles of those components in combination, and more preferably of each of the first and second components, have a particle size of not greater than 10 μm, and especially of not greater than 5 μm. Advantageously, the median particle size of the combined first and second components, and more preferably of each of the first and second components is not more than 10 μm, and preferably not more than 5 μm. The median particle size may be less than 3 μm, for example, about 1.2 μm. It may be desirable in some circumstances for the particles to have a median particle size of at least 0.5 μm. The size of the particles may be calculated by laser diffraction, or by any other method by which the aerodynamic diameter of particles can be determined. "Median particle size" as used herein means mass median aerodynamic diameter ("MMAD"). The MMAD may be determined using any suitable method, for example, using a Multi-Stage Liquid Impinger in accordance with the method described in European Pharmacopoeia (supplement 1999) 2.9.18 (Aerodynamic assessment of fine particles). Alternatively, the size distribution of the particles may be characterised by their volume mean diameter (VMD). Advantageously, the VMD is not more than 10 μm, for example not more than 5 μm, and preferably less than 3 μm. Finely divided dry powders of this kind (which may be described as fumed powders) can be adsorbed onto the surfaces of lung tissue and are believed, in use, to become bound to the epithelium.

A finely divided solid mixture of said first and second components of the medicament (a) may be obtained by size reduction of larger particles by any suitable size reduction method, preferably before mixing. Preferably, the first component of the medicament (a) comprises one or more compounds selected from the group consisting of diacyl phosphatidyl cholines. Examples of suitable diacyl phosphatidyl cholines (DAPCs), are dioleyl phosphatidyl choline (DOPC); distearyl phosphatidyl choline (DSPC) and dipalmitoyl phosphatidyl choline (DPPC). Each of those compounds appears to be capable of forming a thin film or coating on surfaces of the lungs. Most preferably, the first component is DPPC.

The second component may comprise one or more compounds selected from the group consisting of phosphatidyl glycerols (PG); phosphatidyl ethanolamines (PE); phosphatidyl serines (PS); phosphatidyl inositols (PI) and chlorestyl palmitate (CP)

Phosphatidyl glycerol (PG) is believed to be capable of binding to lung tissue and possibly enhancing the binding of the first component and is, therefore, a preferred second component. PG is also a preferred second component because of its ability to form with the first component a very finely-divided, dry powder dispersion in air.

The medicament advantageously comprises a diacyl phosphatidyl choline and a phosphatidyl glycerol. The phosphatidyl glycerol is advantageously a diacyl phosphatidyl glycerol. The acyl groups of the phosphatidyl glycerol, which may be the same or different, are advantageously each fatty acid acyl groups which may have from 14 to 22 carbon atoms. In practice, the phosphatidyl glycerol component may be a mixture of phosphatidyl glycerols containing different acyl groups. The phosphatidyl glycerol is expediently obtained by synthesis from purified lecithin, and the composition of the acyl substituents is then dependent on the source of the lecithin used as the raw material. It is preferred for at least a proportion of the fatty acid acyl groups of the phosphatidyl glycerol to be unsaturated fatty acid residues, for example, mono- or di-unsaturated C18 or C20 fatty acid residues. Preferred acyl substituents in the phosphatidyl glycerol component are palmitoleoyl, oleoyl, linoleoyl, linolenoyl and arachidonoyl. The medicament preferably comprises dipalmitoyl phosphatidyl choline and phosphatidyl glycerol, with the phosphatidyl moiety of the phosphatidyl glycerol advantageously being obtainable from the phosphatidyl moiety of egg lecithin.

The first and second components of the medicament (a) may be present in a weight ratio of from 1:9 to 9:1. Advantageously, the proportion by weight of the first component exceeds that of the second component. Preferably, said first component and said second component are present in a weight ratio of from 6:4 to 8:2. At a weight ratio of about 7:3, the mixture spreads rapidly at a temperature of 35° C. or above.

DPPC can be prepared synthetically by acylation of glycerylphosphorylcholine using the method of Baer & Bachrea—Can. J. Of Biochem. Physiol 1959, 37, page 953 and is available commercially from Sigma (London) Ltd. The PG may be prepared from egg phosphatidylcholine by the methods of Comfurions et al, Biochem. Biophys Acta 1977, 488, pages 36 to 42; and Dawson, Biochem J. 1967, 102, pages 205 to 210. When co-precipitated with DPPC from a common solvent such as chloroform, PG forms with DPPC a fine powder which spreads rapidly over the surfaces of the airways and lungs. The most preferred composition of the invention contains DPPC and a phosphatidyl glycerol derived from egg phosphatidyl choline and having a mixture of C16, C18 (saturated and unsaturated) and C20 (unsaturated) acyl groups. One form of that composition is obtainable from Britannia Pharmaceuticals Ltd., 41–51 Brighton Road, Redhill, Surrey, under the trade mark "ALEC". For use in the device of the present invention, however, it is preferred for the particle size of the mixture to be less than that of "ALEC" in the form in which it is currently obtainable commercially. To obtain a mixture in which the particle size is suitable for use in the device of the invention, the phospholipid components may be dissolved in a suitable solvent, for example ethanol, the solution filtered and vacuum-dried, and the solid product size-reduced to obtain particles of the desired size. During size-reduction, care should be taken to protect the mixture from moisture, oxygen, direct heat, electrostatic charge and microbial contamination.

"Antiasthma drug" is used herein to include any drug which has biological activity against asthma. It will be appreciated that, as used herein, "antiasthma drug" is to be understood as not including the compositions of the medicament of ingredient (a). The antiasthma drug may comprise one or more respiratory drugs including but not limited to drugs selected from the group consisting of $\beta_2$-agonists, steroids, cromones, antimuscarinic drugs and leukotriene receptor antagonists. The combination product may comprise one or more said antiasthma drugs in an amount of up to 10 parts, especially up to one part by weight per hundred parts by weight of said first and second components, in combination, of the said medicament (a). It will be appreciated that the respiratory drug or drugs should be present in such an amount that each dose delivered by the device contains an effective amount of the drug or drugs.

The combination product may comprise a $\beta_2$-agonist which may be terbutaline, a salt of terbutaline, for example terbutaline sulphate, or a combination thereof or may be salbutamol, a salt of salbutamol or a combination thereof. Salbutamol and its salts are widely used in the treatment of respiratory disease. The active particles may be particles of salbutamol sulchate. Long-acting $\beta_2$ adrenoceptor agonists may be present, for example, formoterol, salmeterol, and salts thereof.

The combination product may comprise an antimuscarinic drug, for example ipatropium bromide.

The combination product may comprise a steroid, which may be, for example, beclomethasone dipropionate, budesonide, triamcinolone acetonide or may be fluticasone. The medicament may comprise other prophylactic drugs, including cromones, for example, sodium cromoglycate or nedocromil. The medicament may include a leukotriene receptor antagonist.

Advantageously, at least ingredient (a) is arranged to be delivered to a patent in the form of at least one individual inhalable dose, the or each individual dose comprising said first and second components of ingredient (a) in a combined amount of at least 10 mg. Whereas phospholipids have been disclosed previously as adjuvants in certain forms of delivery device, the amounts of phospholipid administered in a dose by those previously disclosed devices have been much smaller than those envisaged according to the present invention. In fact, it is preferred in accordance with the present invention for each individual dose to comprise at least 25 mg, and more especially at least 40 mg of said first and second components. The first and second components are substantially non-toxic, and the upper limit of the dosage of ingredient (a) may therefore in general be selected having regard to convenience taking into account matters such as, for example, the comfort of the patient and/or design parameters of the device. In general, however, the device will be suck that it can deliver doses of up to 1000 mg, advantageously up to 500 mg, preferably up to 200 mg, and especially up to 100 mg. Preferably, at least ingredient (a) is arranged for sequential delivery of a multiplicity of inhalable doses.

The products of the invention have the further advantage that the first and second components of the medicament (a) may be of synthetic origin. It has been found undesirable to expose asthmatic patients to proteins of animal origin, because such proteins can have a sensitising effect on such patients, and thus the use of synthetic material has considerable advantages over the use of surfactants of animal origin that may contain animal protein.

Because it is desirable in the present invention to achieve a relatively long term adsorption of the medicament (a) on the lung surface, it is highly desirable that the medicament (or any active components) should not break down in the environment of the lungs. One of the factors which will reduce the life of a lining or coating will be the presence of enzymes, such as phospholipase A, capable of digesting DPPC and/or PG. Such enzymes only attack the laevorotatory (L) form, which constitutes the naturally occurring form. Therefore, the medicament should preferably contain the dextrorotatory (D) form or at least comprise a racemic mixture, which is obtained by synthetic routes. Suitable dispersion devices may employ a propellant such as a halocarbon to form the gas stream and may include a tapered discharge nozzle baffle or a venturi to accelerate particles through a discharge nozzle, and to remove oversized particles. Suitable halocarbons include hydrofluorocarbons, hydrofluorochlorocarbons and fluorochlorocarbons having a low boiling point, such as those marketed under the trade mark "Freon". The medicament may be packaged with a propellant in a pressurised aerosol container within the inhaler. Other inhalers have an impeller which mixes the powder into an air stream and delivers the powder-laden air into the patient's airways see, e.g. U.S. Pat. No. 5,577,497.

A preferred method and apparatus for administering the medicament (a) involves dispersing the powdered medicament in a propellant gas stream. For example, a pressurised canister of a liquefied gas may be connected to a vial containing the medicament. By releasing controlled amounts of gas from the canister into the vial, increments of the medicament are ejected from the vial as a cloud of powder and may be inhaled by the user. Where compatible with the characteristics of the antiasthma drug to be co-administered, that drug may be introduced into the gas stream, so that it is administered in admixture with the medicament (a). It is envisaged that, in use, one or two inhalable doses of the medicament (a), each dose containing 50 mg, may be administered up to three times daily.

Where the antiasthma drug is to be administered separately and sequentially with the medicament (a) administration of the antiasthma drug may occur as and when required by the patient and the timing of administration may thus be independent of the timing of administration of the medicament (a).

The present invention provides a delivery device for administering to a patient by inhalation a medicament for the prevention or treatment of asthma, the delivery device containing a medicament comprising a surface active phospholipid (SAPL) composition in finely divided form, the SAPL including a component which enhances the spreading of the medicament and the delivery device being capable of delivering of at least one individual dose in an amount of at least 10 mg.

The invention also provides a delivery device for administering to a patient by inhalation a medicament for the prevention or treatment of asthma, the delivery device containing a medicament, the medicament being in finely divided powder form and comprising a first component consisting of one or more phosphacidyl cholines and a second component consisting of one or more compounds selected from the group consisting of phosphatidyl glycerols, phosphatidyl ethanolamines, phosphatidyl serines, phosphatidyl inositols and chlorestyl palmitate, the delivery device being arranged for delivery of at least one individual inhalable dose, the or each individual dose comprising said first phospholipid component and said second component in a combined amount of at least 10 mg.

Furthermore, the invention provides use of (a) a surface active phospholipid (SAPL) composition in finely divided form conjointly with (b) an antiasthma drug in the manufacture of a medicament for the control of asthma.

One form of dispenser according to the invention will now be described in detail, by way of illustration, with reference to the accompanying drawings, in which.

Figure 1:
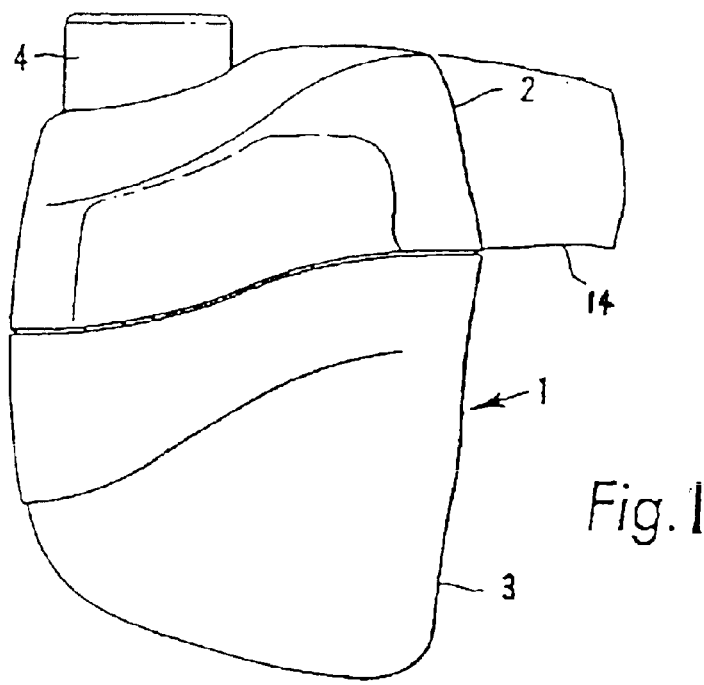
FIG. 1 is a side elevation of a delivery device.
Figure 2:
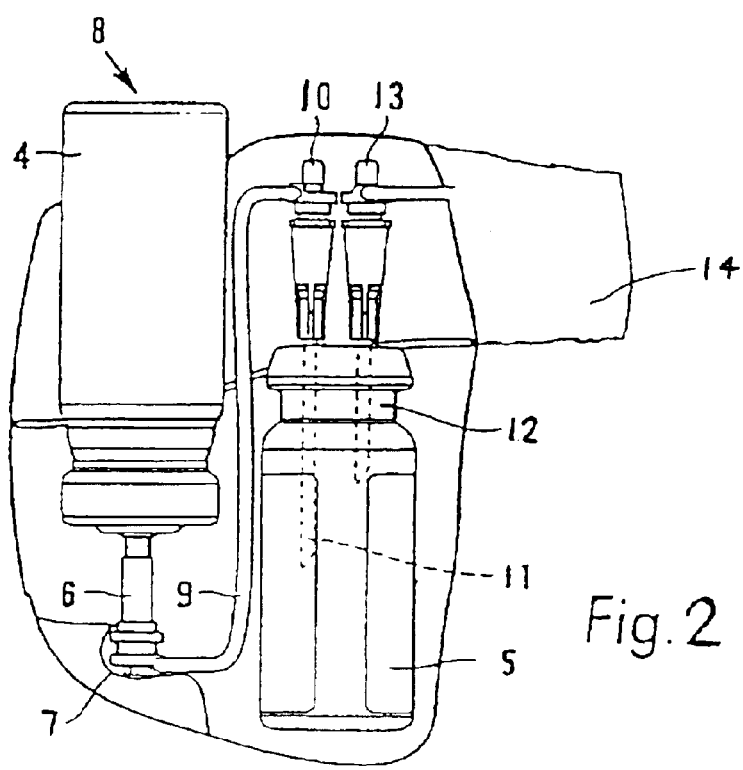
FIG. 2 is a similar view, but shows its interior.

In the drawings, a casing 1 is formed from two plastic mouldings 2 and 3 which snap together to form a container for a pressurised canister 4 and a vial 5. Canister 4 contains a low boiling liquid, preferably a hydrofluorocarbon such as HFA-134a or HFC-227, under sufficient pressure to maintain the propellant liquid at normal room temperature. Vial 5 contains the powdered medicament (a), such as "ALEC". Canister 4 has a release valve 6 which is received in a recess 7 so that finger pressure on the inverted end 8 of the canister will cause propellant to be released into a tube 9. Tube 9 is typically a hard plastics, e.g. pvc or polypropylene, tube of about 2–3 mm outside diameter and about 0.5 to 2 mm inside diameter. Tube 9 connects valve 6 with a fitting 10 and thence to a tube or needle 11 which extends into the vial 5. Vial 5 may be closed with a rubber seal which is penetrated by the tube or needle 11 and self-seals around the tube or needle. A second needle or tube 12 extends part way into the vial through the rubber seal in the neck of the vial and connects with a fitting 13. Fitting 13 discharges into a mouthpiece 14 which is a comfortable shape for the user to place in the mouth. When the patient is in need of medication, he places the mouthpiece 14 into his mouth and breaths and simultaneously depresses the canister 4. This causes a cloud of medicament to be dispensed into the patient's airways. Fittings 10 and 13 may be valves. Valves 10 may be set to permit measured quantities of propellant to enter the vial. Similarly, valve 13 may be set to release when the pressure in the vial reaches a predetermined level. It will be appreciated that the dispenser can be used one-handed in an analogous manner to a conventional nebulizer.

The antiasthma drug may be administered separately from a separate device either immediately before or after administration of the medicament (a), or separately as required by the patient. The antiasthma drug may be dispensed from any suitable form of inhaler device, such as a dry powder inhaler or pressurised metered dose inhaler. Such devices containing antiasthma drugs are well known and widely available commercially, and do not require further explanation.

Instead, in addition to the powdered phospholipid composition, the vial 5 may incorporate other known pulmonary or respiratory medicaments such as salbutamol, Beclomethasone, corticosteroids, or other asthma drugs. It is, however, preferred to package the conventional asthma drug in the propellant canister or in a capsule interposed between the propellant container and the vial containing the phospholipid composition. In this way, the lungs and airways receive a cloud of phospholipid composition and an aerosol of the conventional drug sequentially or simultaneously. This combined therapy gives both quick relief and lasting protection as the film of phospholipid composition spreads over the lung tissue. Instead of packaging the phospholipid composition in a multi-use vial, it may be contained in a capsule, which may be a single use quantity, between the outlet from the propellant canister and the mouthpiece.

Figure 3:
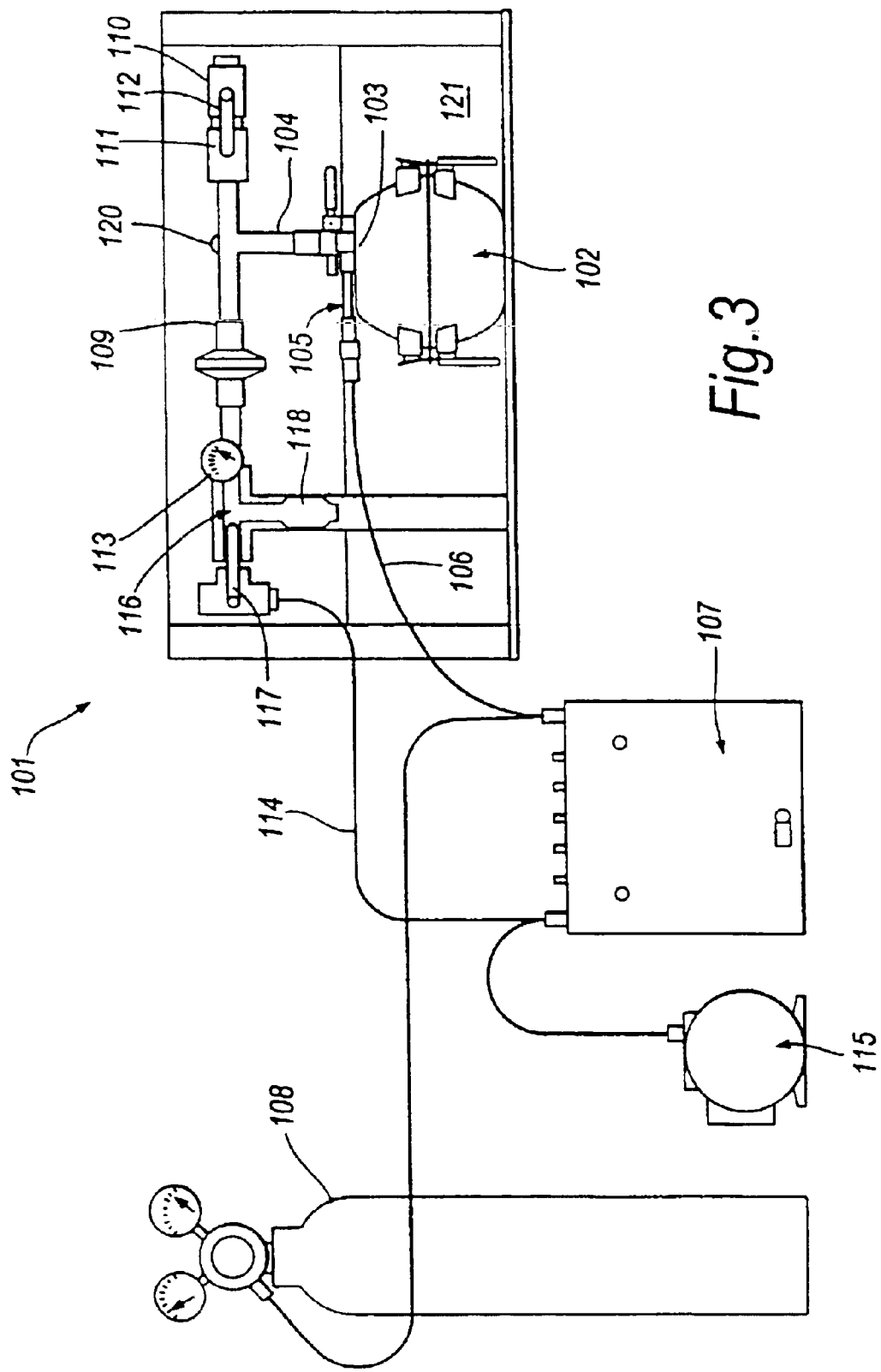
FIG. 3 is a schematic view of another embodiment of delivery device in accordance with the invention.

Another form of delivery device is illustrated in FIG. 3.

Conceptually, the device 101 shown in FIG. 3 provides a receptacle 102 having a volume of several liters which is filled with aerosolubilized solid SAPL composition, optionally also including an antiasthma drug, and is then inhaled by a patient via a breathing tube 120 connected to a pipe 104 leading from the receptacle. Receptacle 102 1s first evacuated using vacuum pump 115. A quantity of the solid, powdered SAPL composition is contained within a mesh type holder 105 within a tube 106, and air is then introduced through the tube 106 to cause the SAPL powder to form an aerosolubilized cloud within the receptacle 102. When receptacle 102 reaches approximately atmospheric pressure, breathing tube 120 is opened to permit the patient to inhale the SAPL composition.

The device 101 comprises a stainless steel receptacle 102 of volume approximately 4 liters which has an aperture 103 at its top extremity to which a vertically extending pipe 104 is connected. Pipe 104 is connected to a transverse pipe 109 and also a breathing tube 120 which extends through a screen 121, so that the apparatus is not visible to the patient. Breathing tube 120 may be fitted with a plug at its distant end, the plug being removable before use. A mesh holder 105 is mounted on the top of the receptacle 102 as part of a connection between an air line 106 and the receptacle. The mesh holder can be disassembled to introduce a quantity of powdered medicament into the delivery device. One end of the air line 106 is connected, via the mesh holder, to the receptacle 102 via a port 103. The other end of the air line 106 is connected, via control device 107, to a regulated source 108 of compressed is propellant, e.g. air. If desired, the source of compressed propellant can also contain a biologically active component for the treatment of asthma. The pipe 104 extends upwardly from receptacle to meet a horizontally extending pipe 109, from one end of which there extends pipe 110 to atmosphere. A valve 111, openable by means of a handle 112, is provided in the horizontally extending pipe 109, closing off the pipe 110 from the receptacle 102 except when valve 111 is open.

At the other end of the horizontal pipe 109 there is provided a pressure gauge 113. At that end, the horizontal pipe 109 is connected to an air line 114, which extends, via the control device 107, to a vacuum pump 115, which is controllable independently of the control device 107. A valve 116, operable by a handle 117, is provided for the purpose of opening or closing the pipe between the receptacle 102 and the air line 114.

A safety pressure relief valve 118 is incorporated in the apparatus and is preferably arranged to open at 0.034 bar above atmospheric pressure.

In use, micronised SAPL composition (optionally together with an antiasthma drug) may be introduced into the mesh holder device 105, which is then inserted into the port 103 leading into the receptacle 102. On insertion of the mesh holder device, the receptacle is sealed, the valves 111 and 116 both being closed. The pressure inside the receptacle 102 is then reduced by means of opening valve 116 and pumping air out of the receptacle 102 through air line 114.

Control unit 107 may include a needle valve (which may be adjustable) co control the rate at which air is evacuated from the receptacle 102. If pressure falls too rapidly in the receptacle, it may cause the powdered medicament in the mesh holder device to be sucked prematurely into the receptacle. Thereafter, the valve 116 is closed. Whilst the receptacle 102 remains sealed at reduced internal pressure, the regulated compressed air source 108 is actuated temporarily to inject air into the receptacle 102 through the mesh holder device 105. As a consequence, the powder in the mesh holder device 105 becomes aerosolised and enters the receptacle 102. The pressure may be monitored using the pressure gauge 113 and should at this stage be at or slightly below atmospheric pressure.

The plug is then removed from the mouthpiece of the breathing tube and the patient can then inhale the contents of the receptacle by sucking on the mouthpiece end of the breathing tube.

After the inhalation step, the valve 111 may be closed, and the cycle recommenced.

If desired, the quantity of the powder successfully aerosolised may be determined by weighing the mesh and powder before use (the weight of the mesh previously having been determined) and weighing the mesh with any residual powder after use of the device.

As indicated above, an antiasthma drug may be present in the source of compressed propellant, or be placed in the mesh holder device with the SAPL.

If preferred, or if necessitated by the nature of the antiasthma drug to be administered in a combination treatment with the surface active phospholipid composition, the antiasthma drug may be administered separately from another device, for example, a dry powder inhaler or pressurised metered dose inhaler of known kind widely available for he administration of antiasthma drugs.

Determination of Fine Particle Fraction of Phospholipid Composition

As already mentioned, finely divided ALEC for use in the products of the invention may be obtained by dissolving, filtering and vacuum-drying the components and size-reducing the solid product so obtained. The delivery of the size-reduced material was monitored using a Multi-Stage Impinger (MLSI) in accordance with the method described in European Pharmacopoeia (supplement 1999), 2.9.18 (Aerodynamic assessment of fine particles). Vials of the material were loaded on the 5-stage MLSI and delivery of the material tested under a number of operating conditions. Each volume of air drawn of 4l is considered equivalent to one patient inhalation. The results, in Table 1, showed that a relatively large respirable fraction was generated. The respirable (or fine particle) fraction represents particles which reach stages 3, 4 and 5 of the MSLI, indicating a particle size of less than about 5.3 $\mu$m. Such particles are considered to be of a size such that they would enter deep into the lung of a typical patient.

TABLE 1

| Flow Rate Through MSLI (L/min) | Volume of Air Drawn (Litres) | Total Mass of Phos-pho-lipid Loaded (mg) | Mass Delivered into Device (mg) (% of mass loaded) | Mass of Phos-pho lipid MSLI (mg) | Fine Particle Fraction (mg) | Fine Particle Fraction (% ex-device) |
|---|---|---|---|---|---|---|
| 100 | 4 L | 179.1 | 150.3 (84%) | 55.1 | 46.5 | 84.5 |
| 100 | 2 × 4 L | 169.2 | 132.5 (78%) | 60.0 | 45.1 | 75.1 |
| 100 | 3 × 4 L | 162.0 | 133.1 (82%) | 66.0 | 55.7 | 84.4 |
| 100 | 3 L | 136.1 | 119.8 (88%) | 58.6 | 45.1 | 76.9 |
| 100 | 4 L | 129.7 | 107.9 (83%) | 53.0 | 44.7 | 84.3 |
| 100 | 2 × 4 L | 113.5 | 94.0 (83%) | 46.1 | 37.6 | 81.7 |
| 100 | 4 × 4 L | 387.6 | 340.4 (88%) | 117.5 | 86.5 | 73.6 |

Determination of Surface Activity of Phospholipid Compositions

A 2 cm×2 cm platinized grey dipping plate is heated to cherry red using the flame from a Bunsen burner or similar torch. The plate is suspended from an electronic balance capable of weighing up to 500 mg.

To calibrate the apparatus, a small reflon dish is filled with distilled water at approximately 20° C. (room temperature) and placed on a laboratory jack just beneath the dipping plate. The dish is then raised so that the dipping plate just breaks the surface of the water, evenly along the bottom edge. The meniscus drawn up the dipping place is used to set the display of the pen recorder of the electronic balance to read about 73 $mNm^{-1}$ (the air/water surface tension of water at 20° C.). The Teflon dish is lowered, emptied, cleaned, dried and then filled with reagent grade methanol. The dipping plate is cleaned as described above. The dish is then raised so that the dipping plate just breaks the surface of the methanol, evenly along the bottom edge. The meniscus drawn up the dipping plate will cause the pen recorder to read about 22 $mNm^{-1}$ (the air/methanol surface tension of methanol at 20° C.[1]). The Teflon dish is lowered and the dipping plate is cleaned as described above. A zero-reading should be obtained for the cleaned plate alone (i.e. suspended in air).

To obtain a quantitative measure of the surface activity of a material, the Teflon dish is warmed to about 37° C., filled with water at not more than 37° C. and placed on a laboratory jack just beneath the cleaned plate. The dish is then raised so that the dipping plate just breaks the surface of the water, evenly along the bottom edge. The meniscus drawn up the dipping plate will give a reading of about 70 $mNm^{-1}$ (the approximate air/water surface tension of warm water). The material is applied onto the surface of the water using a small spatula. The amount applied should be sufficient to ensure that a complete monolayer has been formed on the surface of the water, such that an excess (as small free-floating particles) can be observed. The surface tension should fall instantly, that fall being recorded by the pen recorder. Equilibrium surface tension readings are taken from the pen recorder after about 1 minute. The temperature of the water in the Teflon dish should be not less than 35° C. immediately after the reading is taken.

The term "high surface activity" as used herein with reference to any composition for use in accordance with the invention means that the equilibrium surface tension as measured in the above method, is at least 10% lower than the surface tension before the composition is applied to the water surface. In practice, the reduction in surface tension obtainable using certain phospholipid compositions such as those mentioned above in illustration of medicament (a) may exceed 50%.

A component included in admixture with another material is to be understood as enhancing the spreading of the other material if, in carrying out the above method for determination of surface activity using the mixture and, separately, using the other material alone, the time taken for the equilibrium surface tension to be reached is shorter for the mixture, as compared to the material alone.

The above method describes determination of surface activity at 37° C. It will be appreciated that, where reference is made herein to enhancing spreading at about normal mammalian body temperature, the method should be carried out at about the normal body temperature of the relevant mammal, where that is not about 37° C.

The following Example illustrates the binding of a preferred phospholipid to the epithelium:

EXAMPLE

Reagents

L-α-Phosphatidylcholine, 1,2—di[1-$^{14}$C]palmitoyl in Toluene:Ethanol (1:1 v/v), 114 mCi/mmol, 50 $\mu$Ci in 2 mL (CFA604 B36, Amersham)
L-α-Phosphatidylcholine, dipalmitoyl (C16:0) (P-6267, Sigma)
DL-α-Phosphatidyl-DL-glycerol, dipalmitoyl (C16:0) (P-5650, Sigma)
Egg Phosphatidylglycerol (Batch 24756, Macfarlan Smith, Ltd.)
Sodium Chloride, 0.9%, B.P. (Baxter Healthcare)
Calcium Chloride (C-4901, Sigma)
Toluene (T-4428, Sigma)
Ethanol, AnalaR (10107.7Y, BDH)
NCS-II Tissue Solubilizer, 0.5N Solution (NNCS-502), Amersham)
OCS Organic Counting Scintillant (NOCS104, Amersham)

In preparation for the dispersions in which the epithelium would be incubated, stock solutions of the phospholipid components were prepared on the first day of Run 1. These solutions were as follows:

L-α-DPPC, 2.4 mg. $mL^{-1}$ in toluene:ethanol, 1:1
DL-α-DPPG, 3.0 mg. $mL^{-1}$ in toluene:ethanol, 1:1
Egg PG, 3.0 mg. $mL^{-1}$ in toluene:ethanol, 1.1

All of the above solutions were stored at 4° C. in glass vials, the threads of which were sealed with teflon tape to minimise evaporation of the solvent. Each glass vial was then placed inside a second, tightly capped glass vial. These solutions were used for each of the five runs in the trial. A solution of 200 mg. $L^{-1}$ $CaCl^2$ in 0.9% saline was also prepared on the first day of Run 2 and was used in each of Runs 2 to 5.

Equipment

Special Ultrasonic Cleaner, Model G112 SP1G (Laboratory Supplies Co. Inc., Hicksville, N.Y., U.S.A.)
VF2 Vortex (IKA-Labortechnik)
Shaking Water Bath, Model TSB2-201-A (Thermoline Scientific Equipment, Smithfield, Australia)
Contherm Series Five, Fan Forced Oven (Contherm Scientific Ltd. Lower Hutt, N.Z.) TRI-CARB 2700TR Liquid Scintillation Analyser (Packard Instrument Co., Meriden, Conn., U.S.A.)
Ultrasonic Cleaner, Model FXPI2 (Unisonics Pty. Ltd. Sydney, Australia)

Bronchial Epithelium

To provide a source of bronchial epithelium, porcine lungs were obtained from an abattoir within 24 h of death. The lungs had been scored at 4° C. since the time of death. The secondary bronchus was dissected from the right and/or left lungs. The exterior surface of the bronchus was trimmed of all lung tissue, and the bronchus was further cut into sections having a known surface area of bronchial epithelium (approximately 0.5 cm×0.5 cm), leaving the epithelium and cartilage intact. The surface of the epithelium was rinsed with 0.9% saline to remove any mucus.

Where necessary sections of bronchial epithelium were stored in 0.9% saline at −20 for 3 to 7 days until required for use. The sections were thawed before use on the first day of each run.

For bronchial epithelium, a total of five runs were is completed. Each run consisted of three groups, as follows:

1. DPPC only
2. DPPC+DPPG
3. DPPC+eqgPG

Four dispersions were prepared on the first day of each run. All groups received both 20.5 μL (3.3 μg) of $^{14}$C-L-α-DPPC and 5.5 μL (13.2 μg) of unlabelled L-α-DPPC from the stock solutions. In addition, Group 2 received 5.5 μL (16.5 μg) DL-α-DPPC, while the same quantity of egg PG was added to Group 3. In Groups 2 and 3, the ratio of total DPPC to PG was 1:1. The phospholipic component was mixed with 6.6 ml of 0.9% saline for Groups 1, 2, and 3. All of the above listed volumes were used when there were two sections of epithelium in each treatment group. When the number of sections was increased, the volumes of all components were increased accordingly, keeping all quantities in the same proportions as above. Table 2 summarises the additives to the incubation mixtures.

TABLE 2

Components of Incubation Dispersions

| Group | Saline | $^{14}$C-L-α-DPPC | L-α-DPPC | DL-α-DPPC | Egg PG |
|---|---|---|---|---|---|
| 1 | X | X | X | | |
| 2 | X | X | X | X | |
| 3 | X | X | X | | X |

To solubilise the phospholipid components in the aqueous medium, each of the four incubation dispersions was sonicated for 45 min, then vortexed to mix for 1 min.

From each dispersion, two lots of 2.8 mL were transferred to two glass vials. A single section of epithelium was incubated in each of these dispersions, so that there were four groups of two sections of bronchial epithelium in each group. Bronchial epithelium was taken from a single pig on any given day of incubation. Incubation was at 37° C. for 24 h in a shaking water bath.

Aliquots of the Group 1 dispersion were transferred to glass scintillation vials and incubated at 37° C. in an oven for the 24 h. These aliquots were used as the standards for the calibration curve. Matching aliquots from the other group dispersions were also taken, and the β-counts from these were compared with those from the group 1 dispersion as a check that all dispersions contained the same quantity of DPPC.

On the second day of each run, the sections of epithelium were removed from the incubation dispersions and were each rinsed 20 times with 0.9% saline, warmed to 37° C. in a water bath, to remove any loosely adhering phospholipid. Care was taken not to mechanically disturb the mucosal surface of epithelium. Each section of bronchial epithelium was then removed from the attached cartilage. The sections of epithelium were further cut into smaller pieces to aid the digestion of the tissue by the solubilising agent which was added in a volume of 1.5 mL to the epithelium in scintillation vials. The same volume of solubiliser was added to each of the standard aliquots and to a blank. All vials were gently shaken to mix the contents and were warmed to 55° C. in a fan-forced convection oven overnight (18–20 h).

On the third day of each run, 10 mL of organic counting scintillant were added to each scintillation vial, and these were vortexed to mix for 30 s.

The β-counts of each sample and standard were measure a using a liquid scintillation analyser. A second count was conducted within 7 h of the first count. If the two counts were similar, only the first count was used to construct the line of calibration and to quantify the samples.

From the line of calibration, the mass of $^{14}$C-DPPC adsorbed to each section of epithelium was calculated. To calculate the mass of total DPPC adsorbed to each section, the mass of $^{14}$C-DPPC was multiplied by 5 since the quantity of $^{14}$C-DPPC in each of the dispersions was ⅕ of the total amount of DPPC. The result is expressed in Table 2 as the total amount of DPPC adsorbed per $cm^2$ of epithelium.

The results in Table 3 show that increased binding of DPPC to bronchial epithelium is observed in the presence of DPPG, but that the extent of binding is improved still further where Egg PG is used instead of DPPG.

While the present invention has been described with particular reference to the treatment of human patients for asthma, it is possible that the invention may also be applicable to the treatment of other pulmonary diseases or conditions such as rhinnitis.

The combination product of the present invention may also be employed in the treatment of pulmonary conditions in other mammals. An example is reactive airway disease in horses.

TABLE 3

| | Total DPPC Adsorbed to Bronchial Epithelium ($\mu g/cm^2$) | | |
|---|---|---|---|
| | DPPC | DPPC:DPPG, 1:1 | DPPC:Egg PG, 1:1 |
| | 0.341 | 0.501 | 0.878 |
| | 0.299 | 0.321 | 0.743 |
| | 0.219 | 0.214 | 0.472 |
| | 0.116 | 0.263 | 0.731 |
| | 0.276 | 0.378 | 0.705 |
| | 0.280 | 0.494 | 0.529 |
| | 0.528 | 0.355 | 0.836 |
| | 0.192 | 0.419 | 0.792 |
| | 0.340 | 0.294 | 0.986 |
| | 0.321 | 0.362 | 0.791 |
| n | 10 | 10 | 10 |
| Mean | 0.291 | 0.360 | 0.746 |
| SD | 0.110 | 0.093 | 0.153 |

What is claimed is:

1. A therapeutic combination product for treatment of asthma comprising:
   (a) a medicament comprising a surface active phospholipid (SAPL) composition in finely divided dry powder form, the SAPL composition including a component which enhances spreading of the medicament over a surface at about normal mammalian body temperature and comprising a first component comprising one or more phosphatidyl cholines and a second component comprising one or more compounds selected from the group consisting of phosphatidyl gylcerols, phosphatidyl ethanolamines, phosphatidyl serines, phosphatidyl inositols and cholesterol palmitate, and
   (b) an antiasthma drug,
wherein ingredients (a) and (b) are provided in a form for administration together and at least ingredient (a) is arranged for delivery of at least one individual inhalable dose, the individual dose or each individual dose comprising said ingredient (a) in an inhalable amount of at least 25 mg, for forming an adsorbed layer of phospholipid extending over the surfaces of the lungs and air passages.

2. A combination product as claimed in claim 1, in which medicament (a) comprises said first component and said second component in a weight ratio of from 1:9 to 9:1.

3. A combination product as claimed in claim 2, in which the proportion by weight of said first component exceeds that of said second component.

4. A combination product as claimed in claim 3, in which said first component and said second component are present in a weight ratio of from 6:4 to 8:2.

5. A combination product as claimed in claim 1, in which the medicament (a) comprises a phosphatidyl glycerol.

6. A combination product as claimed in claim 5, in which the phosphatidyl glycerol comprises one or more diacyl phosphatidyl glycerols, of which at least a proportion of the acyl groups are unsaturated.

7. A combination product as claimed in claim 1, in which the medicament (a) comprises one or more compounds selected from the group consisting of diacyl phosphatidyl cholines.

8. A combination product as claimed in claim 7, in which the medicament (a) comprises dipalmitoyl phosphatidyl choline.

9. A combination product as claimed in claim 1, in which the medicament (a) is in micronised form.

10. A combination product as claimed in claim 1, in which said medicament (a) has a median particle size not exceeding 10 $\mu$m.

11. A combination product as claimed in claim 10, in which said medicament (a) has a median particle size not exceeding 5 $\mu$m.

12. A combination product as claimed in claim 11, in which said medicament (a) has a median particle size of less than 3 $\mu$m.

13. A combination product as claimed in claim 1, in which the antiasthma drug comprises one or more respiratory drugs selected from the group consisting of $\beta_2$-agonists, steroids, cromones, antimuscarinic drugs and leukotriene receptor antagonists.

14. A combination product as claimed in claim 13, which comprises one or more of said antiasthma drugs in an amount of up to 10 parts by weight per hundred parts by weight of said first and second components of medicament (a) in combination.

15. A combination product as claimed in claim 14, which comprises one or more of said respiratory drugs in an amount of up to one part by weight per hundred parts by weight of said first and second components of medicament (a) in combination.

16. A combination product as claimed in claim 13, in which ingredient (b) comprises a $\beta_2$-agonist.

17. A combination product as claimed in claim 13, in which ingredient (b) comprises a steroid.

18. A combination product as claimed in claim 13, in which ingredient (b) comprises a cromone.

19. A combination product as claimed in claim 13, in which ingredient (b) comprises a leukotriene receptor antagonist.

20. A combination product as claimed in claim 13, in which ingredient (b) comprises an antimuscarinic drug.

21. A combination product as claimed in claim 1, wherein the individual dose or each individual dose comprises said ingredient (a) in an inhalable amount of at least 40 mg.

22. A combination product as claimed in claim 1, in which the antiasthma drug is arranged for delivery in admixture with ingredient (a).

23. A method of treatment of asthma, comprising administering to a patient at least one dose of a combination product as defined in claim 1.

* * * * *

UNITED STATES PATENT AND TRADEMARK OFFICE
CERTIFICATE OF CORRECTION

PATENT NO. : 6,824,761 B1
DATED : November 30, 2004
INVENTOR(S) : Hills et al.

It is certified that error appears in the above-identified patent and that said Letters Patent is hereby corrected as shown below:

Title page,
Item [56], References Cited, FOREIGN PATENT DOCUMENTS, after "WO 96/19199 6/1996" please insert -- * --.

Signed and Sealed this

Nineteenth Day of April, 2005

JON W. DUDAS
*Director of the United States Patent and Trademark Office*